United States Patent [19]

Webster, Jr.

[11] Patent Number: 4,960,134

[45] Date of Patent: Oct. 2, 1990

[54] STEERABLE CATHETER

[76] Inventor: Wilton W. Webster, Jr., 5114 Commerce Dr., Baldwin Park, Calif. 91706

[21] Appl. No.: 273,048

[22] Filed: Nov. 18, 1988

[51] Int. Cl.$^5$ .............................................. A61N 1/00
[52] U.S. Cl. .................................. 128/786; 128/642; 128/800
[58] Field of Search ............... 128/642, 783, 784, 785, 128/786, 790, 800, 772; 603/95

[56] References Cited

U.S. PATENT DOCUMENTS

| 3,552,384 | 1/1971 | Pierie et al. | 604/95 |
|---|---|---|---|
| 3,631,848 | 1/1972 | Muller | 604/95 |
| 4,456,017 | 6/1984 | Miles | 128/772 |
| 4,633,880 | 1/1987 | Osypka et al. | 128/642 |
| 4,832,048 | 5/1989 | Cohen | 128/786 |

FOREIGN PATENT DOCUMENTS 2501995 9/1982 France ................... 128/785

Primary Examiner—Lee S. Cohen
Assistant Examiner—S. Getzow
Attorney, Agent, or Firm—Christie, Parker & Hale

[57] ABSTRACT

A catheter, which is adapted to be inserted into a body lumen, comprises a symmetrical cylindrical control handle, an elongate tubular catheter body, and a flexible catheter tip having a lumen offset from the axis of the catheter tip. The control handle comprises a housing having a piston chamber at its distal end. A piston is mounted in the piston chamber and is afforded lengthwise movement. The proximal end of the catheter body is fixedly attached to the distal end of the piston. A puller wire is attached to the housing and extends through the piston, through and coaxial with the catheter body and into the offset lumen of the catheter tip where it is attached to the wall of the catheter tip. Lengthwise movement of the piston relative to the housing results in deflection of the catheter tip.

12 Claims, 2 Drawing Sheets

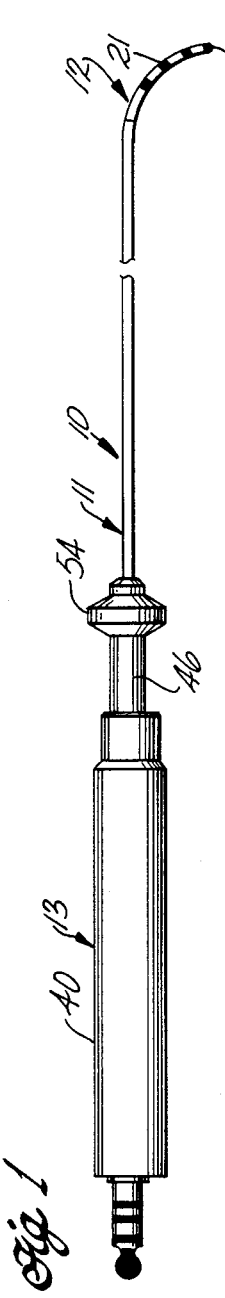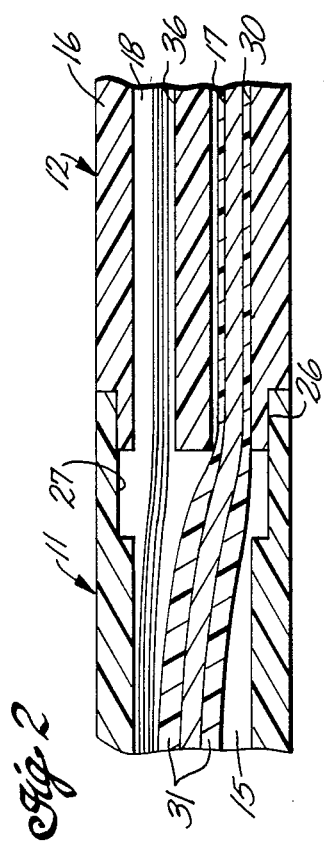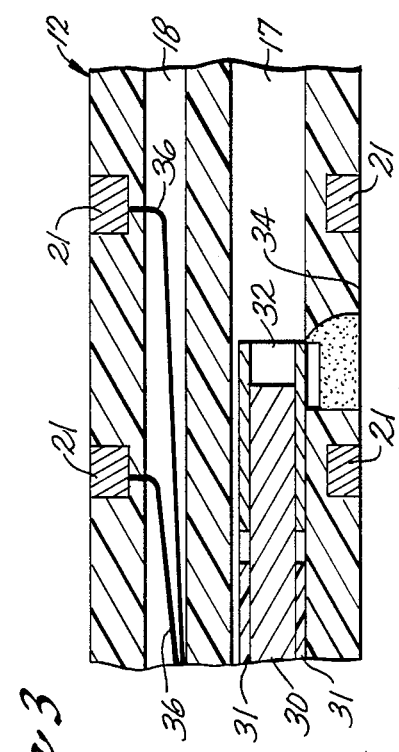

STEERABLE CATHETER

FIELD OF THE INVENTION

This invention relates to steerable catheters for use in a body lumen, and more specifically to a rotatable electrode catheter having a steerable tip.

BACKGROUND OF THE INVENTION

Catheters have been in common use in medical practice for many years. They are used to probe locations inside a body lumen which are otherwise unreachable without surgery. A catheter is first inserted into a major vein or artery, or other body lumen which is near the body surface. The catheter is then guided to the area of concern by further inserting it into the body lumen. As medical knowledge increases, catheterizations have become more complicated and more exacting. In many situations the ability to control the exact position and orientation of the catheter tip largely determines how useful the catheter is.

The body of a catheter is long and tubular. The problem of control over such a device has resulted in catheters which are generally rigid and preformed into specific shapes. This is exemplified by U. S. Pat. No. 3,485,234 to Stevens, which describes a method for making a catheter in any desired shape. However, given the complexity of body lumens, each preformed catheter can only reach certain areas. Thus, for many examinations, multiple catheters are needed, either inserted together or each one in turn. In either case, this greatly adds to the complexity of the procedure and create additional risk for the patient.

Flexible catheters having steerable tips are also known. Such catheters have control handles at their proximal ends controlling the tips. U. S. Pat. No. 4,586,923 to Gould describes many of these. The mechanisms described involve control handles which are asymmetrical. This results in the control handle being less effective when it is rotated, as the controls are no longer in a convenient position to use. Control of the catheter is therefore limited, as the user is not free to rotate the device without losing some control over it.

A catheter often has probes of some kind, e.g., electrodes, on its tip in order to deliver stimuli and/or take measurements within the body lumen. In such a catheter, the probe is electrically connected to an instrument capable of generating the stimuli or recording and/or interpreting signals received by the probes. The connection to this additional instrument generally involves the use of multiple wires which plug into separate sockets, as shown in U. S. Pat. No. 4,603,705 to Speicher, or the use of a single multiple pin plug which fits into a corresponding multiple pin socket. In either case, if the catheter is rotated, the connections must be unplugged and reset, since they otherwise restrict the movement of the catheter. This problem further increases the risks mentioned above in regards to multiple catheters. Each catheter has its own connections, all of which will need to be reset as the catheters are manipulated. The additional loss of data flow and increased procedure length further increase the risk to the patient.

SUMMARY OF INVENTION

This invention therefore provides a steerable catheter having a symmetrical control handle which can be rotated freely while in use. The catheter comprises an elongated catheter body having a first lumen which extends through the catheter body. The catheter tip is fixedly attached to the distal end of the catheter body. The catheter tip comprises a lumen which is offset from the axis of the catheter tip.

A control handle is attached to the proximal end of the catheter body. The control handle comprises a generally symmetrical housing having a piston chamber at its distal end. A piston having a longitudinal and preferably axial bore is mounted within the chamber and is manually movable lengthwise within the chamber. The proximal end of the catheter body is fixedly attached to the distal end of the piston.

An elongated puller wire is fixedly attached to the control handle housing at a location proximal to the piston and extends through the bore of the piston, through and preferably coaxial with the lumen of the catheter body and into the off-axis lumen of the catheter tip. The distal end of the puller wire is fixedly attached to the wall of the catheter tip. In such an arrangement, movement of the piston relative to the housing causes movement of the puller wire relative to the catheter body and catheter tip, resulting in deflection of the catheter tip.

In a preferred embodiment of the invention, the catheter tip comprises one or more electrodes. Lead wires extend from the control handle through the lumen of the catheter body, preferably through a lumen in the catheter tip, and preferably a second off-axis lumen, and are there electrically connected to the electrodes.

In the control handle, the electrode leads extend through the bore of the piston and through the housing of the control handle to an electrical connector for connecting the leads to a electrical stimulator and/or recorder. In such an embodiment, it is preferred that the connector is a rotary connector to afford rotatable movement to the control handle and catheter without breaking electrical contact with the stimulator and/or recorder.

BRIEF DESCRIPTION OF THE DRAWINGS

These and other features and advantages of the present invention will be better understood by reference to the following detailed description when considered in conjunction with the accompanying drawings wherein:

FIG. 1 is a longitudinal cross-sectional external view of a preferred electrode catheter constructed in accordance with the present invention;

FIG. 2 is an enlarged view of the junction of the catheter body and the catheter tip;

FIG. 3 is an enlarged cross-sectional view of the catheter tip showing the attachment of the puller wire.

DETAILED DESCRIPTION

Figure 4:
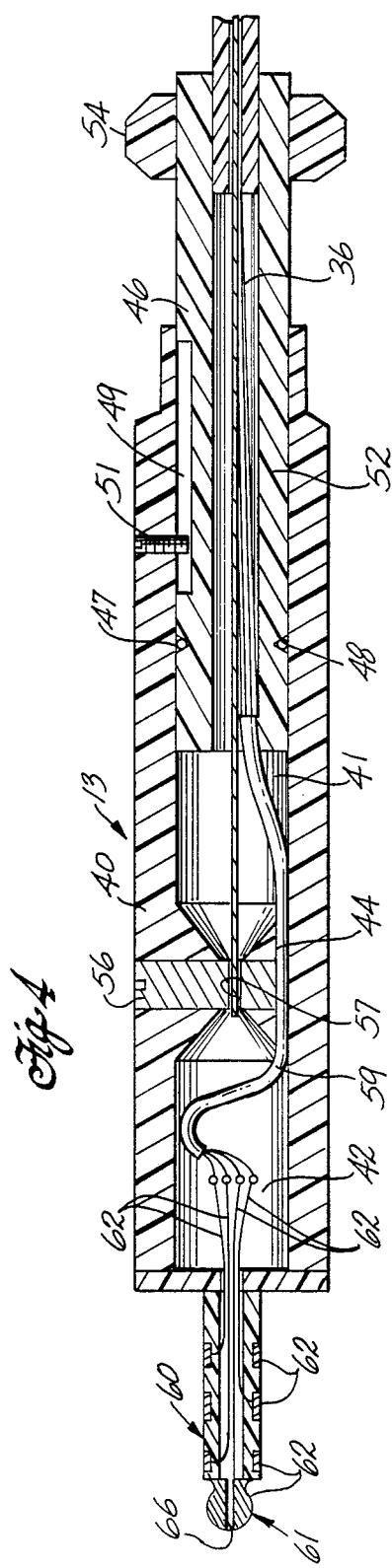
FIG. 4 is an enlarged longitudinal cross-sectional view of the control handle.

FIG. 1 illustrates a preferred electrode catheter constructed in accordance with the present invention. The electrode catheter 10 comprises an elongated catheter body 11 having proximal and distal ends, a catheter tip 12 at the distal end of the catheter body 11, and a control handle 13 at the proximal end of the catheter body 11.

The catheter body 11 comprises an elongated, tubular construction section having a single lumen 15. The catheter body 11 is flexible, i.e., bendable, but substantially non-compressible along its length. The catheter body 11 may be of any suitable construction and made of any suitable material. A presently preferred construction comprises a nylon tube surrounded by braided stainless steel with a polyurethane coating.

The length and diameter of the catheter body 11 are not critical and may vary according to the application. For the electrode catheter shown in the accompanying drawing, a length of about 48 inches, an outer diameter of about 0.09 inch, and an inner diameter, i.e. lumen diameter, of about 0.03 to about 0.04 inches is presently preferred.

The catheter tip 12 comprises a short section of flexible tubing 16 having a pair of nonoverlapping, e.g., side-by-side first and second lumens 17 and 18 which are off-axis, i.e., are not coaxial with catheter tip 12. The tubing 16, may be made of any suitable materials, and is preferably more flexible than the catheter body. A presently preferred material for the catheter tip is polyurethane having a D55 hardness.

The diameter of the catheter tip 12 is not critical, but is preferably about the same as, or slightly smaller, than the diameter of the catheter body 11. The length of the catheter tip 12 is likewise not critical. The embodiment shown, the length of the catheter tip 12 is about two inches.

Along the length of the flexible tubing 16, there are a plurality of electrodes 21. The electrodes 21 are in the form of metal rings, the outer diameter of the electrodes 21 being about the same as the outer diameter of the flexible tubing 16 so that the electrodes 21 form a smooth, continuous surface with the outer surface of the flexible tubing 16. A rounded end electrode 22 is positioned at the distal end of the catheter tip 12.

A preferred means for attaching the catheter tip 12 to the catheter body 11 is shown in FIG. 2. The proximal end of the catheter tip 12 comprises an outer circumferential notch 26 and the distal end of the catheter body 11 comprises an inner circumferential notch 27. The notches 26 and 27 are sized to allow the notched proximal end of the catheter tip 12 to be snugly inserted into the notched distal end of the catheter body 11. The catheter tip 12 is then fixedly attached to the distal end of the catheter body 11 by glue or the like. As shown, the lumen 15 of the catheter body 11 is in communication with both off-axis lumens 17 and 18 of the catheter tip 12.

A puller wire 30, preferably made of stainless steel, extends from the control handle 13 through the lumen 15 of the catheter body 11 and into the first lumen 17 of the catheter tip 12. The puller wire 30 extends into the first lumen 17 of the catheter tip 12 to a position near the distal end of the catheter tip 12 and is fixedly attached to the wall of the flexible tubing 16. The puller wire 30 is preferably surrounded by a teflon sheath 31 or the like for lubricity and to keep the puller wire 30 generally coaxial with the catheter body 11. In the first lumen, the sheath 31 is swaged, i.e., thinned to smaller wall thickness to accommodate the smaller first lumen 17 of the catheter tip 12.

A preferred means for attaching the puller wire 30 to the wall of the catheter tip is shown in FIG. 3 and comprises a short piece of tubular stainless steel 32, e.g., hypodermic stock, which is fitted over the distal end of the puller wire 30 and crimped to fixedly secure the puller wire 30. The distal end of the tubular stainless steel 32 is fixedly attached, e.g., by welding, to a stainless steel crosspiece 33 such as stainless steel ribbon or the like. The crosspiece 33 sits within a notch 34 in the wall of the flexible tubing 16 which extends into the first lumen 17. This provides an opening through the wall of the flexible tubing 16 into the first lumen 17. The stainless steel crosspiece 34 is larger than the opening and, therefore, cannot be pulled through the opening. The portion of the notch 34 not filled by the crosspiece 33 is filled with glue or the like, preferably a polyurethane glue harder than the material of the flexible tubing 16. Rough edges, if any, of the crosspiece 34 are polished to provide a smooth, continuous surface with the outer surface of the flexible tubing 16.

Electrode lead wires 36 extend from the control handle 13 through the lumen 15 of the catheter body 11 and into the second lumen 18 of the catheter tip 12. The lead wires 36 are attached to the electrodes 21 and 22 by any conventional technique.

With reference to FIG. 4, the control handle 13 comprises a generally cylindrical housing 40 having open chambers at each end. A piston chamber 41 is at the distal end of the housing 40, and a connector chamber 42 is at the proximal end of the housing 40. There is an axial passageway 43 and an offset passageway 44 leading from the piston chamber 41 to the connector chamber 42. The housing is generally symmetrical about its longitudinal axis. This allows the control handle to be freely rotated without altering convenience or quality of control.

A cylindrical piston 46 is slidably disposed within and generally coaxial with the piston chamber 41. The piston 46 comprises a circumferential O-ring notch 47 which carries an O-ring 48 to provide a snug, watertight fit between the piston 46 and the wall of the piston chamber 41.

The piston 46 further comprises a slot 49 extending along a portion of its length proximal to the O-ring notch 47. When the piston 46 is disposed within the piston chamber 41, a pin 51, e.g. a set screw, extends from the wall of the housing 40 into the slot 49. The piston 46 can slide distally until the pin 51 engages the proximal end of the slot 49 and proximally until the pin 51 engages the distal end of the slot 49. Thus, the pin 51 and slot 49 limit lengthwise movement of the piston 46 within the piston chamber 41 and prevent the piston 46 from being pushed out of the piston chamber 41.

The piston 46 has an axial bore 52 along its length. The diameter of the axial bore 52 is about the same as the outer diameter of the catheter body 11. The catheter body extends into the axial bore 52 and is fixedly attached, e.g. by glue, to the piston 46.

The distal end of the piston 46 extends beyond the distal end of the housing 40, in order that it may be manually controlled by the user. An annular thumbrest 54 is attached to the distal end of the piston 46 to facilitate lengthwise movement of the piston 46.

The puller wire 30 extends through the axial bore 52 of the piston 46 and is fixedly attached to the housing 40 by means of an anchor 56. The anchor 56 extends into a transverse hole in the portion of the housing 40 between the connector chamber 42 and piston chamber 41. The anchor 56 blocks the axial passageway 43, but not the offset passageway 44. The anchor 56 is rotatable within the hole, but fits snugly so that it does not rotate freely.

The anchor 56 comprises a transversely extending hole 57 which can be rotated into alignment with the axial passageway 43. To secure the puller wire 30 to the anchor 56, the puller wire 30 is passed through the axial passageway 43 and transversely extending hole 57 in the anchor 56 and the anchor 56 is rotated to wedge the puller wire 30 between the anchor 56 and the wall of the housing 40. Tension on the puller wire 30 can be adjusted by rotation of the anchor 56.

In use, the catheter tip can be curved or bent to steer the tip into a branching lumen, e.g., a branching blood vessel, by gripping the control handle housing and moving the piston distally out of the piston chamber by pushing outwardly on the thumbrest. Because the catheter body is attached to the piston and the puller wire is attached to the housing, this action causes movement of the puller wire relative to the catheter body and tip, effectively pulling the catheter tip proximally toward the catheter handle. Because the puller wire is offset from the axis of the tip, the tip bends in the direction of the offset, as shown in FIG. 1, to accommodate the force exerted on it.

In use, catheters are often rotated slowly as the catheter is passed through a body lumen, e.g. artery. The rotation facilitates passage around bends in the body lumen. The symmetrical design of the handle provides the unique advantage of allowing the handle to be rotated without affecting or altering the manner in which the handle is gripped and manipulated by the physician. Such a design thus facilitates the smooth manipulation of the catheter.

Another unique advantage is provided by maintaining the puller wire in coaxial relation with the catheter body. Often a catheter is inserted into a body lumen and is bent or curved because the body lumen curves or bends. In such a situation, a puller wire which is offset from the axis of the catheter body tends to predispose the catheter in a curved shape wherein the puller wire lies on the inside of the curve. Such a catheter acts like a preformed catheter, i.e. a catheter having a preformed shape, and resists rotation. This is because in such an arrangement, the length of the puller wire is less than the on-axis length of the catheter. This means that rotation of the catheter one-half turn requires the puller wire to move to the outside of the curve. To do this, however, the on-axis length of the catheter must be compressed or reduced relative to the length of the puller wire. Thus, before the tip rotates, the handle must be rotated sufficiently to build sufficient torque to supply the energy required to compress the catheter body. The result is that rotation of the tip lags far behind rotation of the handle which makes control of the tip difficult.

By maintaining the puller wire in coaxial relation with the catheter body in accordance with the present invention, the length of the puller wire and on-axis length of the catheter body are the same, whether the catheter body extends around a curve or not. In this arrangement, less energy is required for rotation of the catheter tip. This allows the tip to be more responsive to rotation of the handle and therefore more easily controlled.

The electrode lead wires 36 extend from the catheter body 11 proximally through the axial bore 52 of the piston 46, the piston chamber 41, the offset passageway 44 between the piston and connector chambers 41 and 42, and into the connector chamber 42. A teflon sheath 59 surrounds and protects the electrode lead wires 36 in the piston chamber 41, offset passageway 44 and connector chamber 42. Within the piston chamber 41, or more preferably the connector chamber 42, the lead wires 36 and sheath 59 are bowed or looped to provide slack as the catheter is manipulated.

In the connector chamber 42, the lead wires 36 are connected to a rotary connector 60. The rotary connector 60 comprises a cylindrical male plug 61 extending proximally from the control handle housing 40 coaxially with the housing 40. The plug 61 is of conventional design and has a series of electrical contacts or terminals 62 along its length, each of which is electrically connected to a separate lead 62, and, therefore, a separate lead wire 36, within the connector chamber 42. These terminals operate independently to allow separate electrical signals to be transmitted through the connector 60 simultaneously. The plug may be inserted directly with a stimulator/recorder or other electrical device or more preferably, connected to the female end to a floating extension cable which in turn has a node plugged to its opposite end which can be plugged into the electrical device.

In the embodiment shown, the catheter tip 12 carries four electrodes and the rotary has four terminals. It is understood that the number of electrodes and terminals may vary as required. Due to its symmetry, the rotary connector 60 can continuously convey electrical signals while the control handle 13 is rotated. This allows greater freedom of movement of the catheter and particularly the control handle without needing to reset the electrical connections and risk losing data.

An annular flange 64 secures the rotary connector 60 to the housing 40 and seals the proximal end of the connector chamber 42. Preferably, there is a vent 66 leading from the connector chamber 42. The vent 66 can be through the housing wall, flange 64 or through the plug 61 of the rotary connector as shown.

The preceding description has presented with reference to a presently preferred embodiment of the invention shown in the drawings. Workers skilled in the art and technology to which this invention pertains will appreciate that alterations and changes in the described structures can be practiced without meaningfully departing from the principal, spirit, and scope of this invention.

For example, it is apparent that the invention is applicable to catheters other than electrode catheters. In such other embodiments, there may be no need for an electrical connector at the proximal end of the control handle. Such other catheters may be designed, for example, to deliver medications, or the like, to a particular location in a body lumen or to take fluid samples from a particular location. In such an embodiment, a continuous lumen may extend through the housing, piston, catheter body, and catheter tip. Other catheters to which this invention is applicable may include, for example, an optic fiber for viewing the lumen or for delivering laser irradiation to the lumen, e.g. to remove plaque in a blood vessel.

It is also apparent that, if the catheter is an electrode catheter, the number, size and location of the electrodes may vary. Moreover, the rotary connector may, for convenience, include a cord extending between the control handle housing and the male plug of the connector. Such an embodiment is preferred if it is desired that the handle not be adjacent the stimulator and/or recorder.

The design of the catheter may vary in other respects. For example, the number of lumens in the catheter body and/or catheter tip may vary as desired. It is preferred that the puller wire be coaxial with the catheter body. To facilitate this, the electrode lead wires may be wrapped around the puller wire sheath rather than extending to one side as shown in the drawing.

While it is preferred that the handle be symmetrical about its longitudinal axis to enable easy manipulation of the handle while being rotated, it is understood that nonsymmetrical variations may be used if desired. Likewise, it is understood that any suitable method for attaching the puller wire to the catheter tip and to the control handle housing may be used.

Accordingly, the foregoing description should not be read as pertaining only to the precise structures described and shown in the accompanying drawings, but rather should be read consistent with and as support to the following claims which are to have their fullest and fair scope.

What is claimed is:

1. A steerable catheter comprising:
   a flexible, elongated catheter body having proximal and distal ends and a first lumen;
   a flexible catheter tip fixedly attached to the distal end of the catheter body, said tip comprising a second lumen, the axis of the second lumen being offset from the axis of the tip;
   a control handle at the proximal end of the catheter body, said control handle comprising:
      a housing having proximal and distal ends and a piston chamber at its distal end;
      a piston having proximal and distal ends and a longitudinal bore therethrough mounted in the piston chamber of the housing and moveable longitudinally within the piston chamber, wherein the proximal end of the catheter body is fixedly attached to the distal end of the piston; and
      means proximal to the piston, for securing the proximal end of a puller wire to the housing;
   an elongated puller wire having a proximal end fixedly attached to the securing means at a location proximal to the piston chamber, said puller wire extending through the bore of the piston, the first lumen of the catheter body and into the second lumen of the catheter tip, said puller wire further comprising a distal end fixedly attached to the catheter tip; and
   whereby longitudinal movement of the piston relative to the housing results in deflection of the catheter tip.

2. A catheter as claimed in claim 1 wherein the puller wire is generally coaxial with the catheter body.

3. A catheter as claimed in claim 1 wherein the distal end of the piston extends out of the distal end of the housing and comprises a thumbrest to facilitate manual movement of the piston relative to the housing.

4. A catheter as claimed in claim 1 wherein the piston comprises a circumferential notch along its length, and the control handle comprises an O-ring positioned within the notch for forming a generally water-tight seal between the piston and the housing.

5. A catheter as claimed in claim 1 wherein the piston comprises a slot along a portion of its length, and the control handle comprises a pin which extends from the housing into the slot.

6. A catheter as claimed in claim 1 wherein the housing comprises a transversely extending bore proximal to the piston, and the securing means comprises an anchor positioned within the bore, said anchor having a hole through which the puller wire extends, and wherein the anchor is rotatable to thereby wedge and secure the proximal end of the puller wire between the anchor and the housing.

7. A steerable electrode catheter comprising:
   a flexible, elongated catheter body having proximal and distal ends and a lumen;
   a flexible catheter tip fixedly attached to the distal end of the catheter body, said tip comprising at least one electrode and at least one lumen having an axis offset from the axis of the tip;
   a control handle at the proximal end of the catheter body, said control handle comprising:
      a housing having proximal and distal ends and a piston chamber at its distal end and a connector chamber at its proximal end;
      a rotary connector attached to the proximal end of the housing, the rotary connector comprising:
         a male plug having a terminal for electrical connection with each electrode; and
         a contact which extends into the connector chamber electrically connected to each terminal;
      a piston having proximal and distal ends and a longitudinal bore therethrough mounted in the piston chamber of the housing and moveable longitudinally within the piston chamber, wherein the proximal end of the catheter body is fixedly attached to the distal end of the piston; and
      means proximal to the piston, for securing the proximal end of a puller wire to the housing;
      an elongated puller wire having a proximal end secured to the securing means, said puller wire extending through the bore of the piston, through the first lumen of the catheter body in generally coaxial relation to the catheter body and into the offset lumen of the catheter tip, said puller wire further comprising a distal end fixedly attached to the catheter tip whereby longitudinal movement of the piston relative to the housing results in deflection of the catheter tip; and
      an electrode lead associated with each electrode, each electrode lead having a distal end attached to an electrode and extending through the catheter tip, catheter body, and piston and into the connector chamber of the housing wherein the electrode lead is attached to a contact of the rotary connecter.

8. A catheter as claimed in claim 7 wherein the distal end of the piston extends out of the distal end of the housing and comprises a thumbrest to facilitate manual movement of the piston relative to the housing.

9. A catheter as claimed in claim 7 wherein the piston comprises a circumferential notch along its length and the control handle comprises an O-ring positioned within the notch for forming a generally water-tight seal between the piston and the housing.

10. A catheter as claimed in claim 7 wherein the piston comprises a slot along a portion of its length and the control handle comprises a pin which extends from the housing into the slot.

11. A catheter as claimed in claim 7 wherein the housing comprises a transversely extending bore proximal to the piston and the securing means comprises an anchor positioned within the bore, said anchor having a hole through which the puller wire extends, and wherein the anchor is rotatable to thereby wedge and secure the proximal end of the puller wire between the anchor and housing.

12. A catheter as claimed in claim 7 wherein the rotary connector comprises a flexible cord between the contacts and the male plug.

* * * * *